United States Patent
Gerold et al.

(10) Patent No.: US 10,166,045 B2
(45) Date of Patent: Jan. 1, 2019

(54) ORTHOPEDIC EXTERNAL FIXATION DEVICE

(71) Applicant: Fixx Orthopedics, LLC, Monticello, MN (US)

(72) Inventors: Thomas Gerold, Monticello, MN (US); Marc Egeland, Minneapolis, MN (US); Kenneth Noonan, Madison, WI (US)

(73) Assignee: Fixx Orthopedics, LLC, Monticello, MN (US)

( * ) Notice: Subject to any disclaimer, the term of this patent is extended or adjusted under 35 U.S.C. 154(b) by 50 days.

(21) Appl. No.: 15/053,154

(22) Filed: Feb. 25, 2016

(65) Prior Publication Data

US 2016/0249952 A1 Sep. 1, 2016

Related U.S. Application Data

(60) Provisional application No. 62/121,904, filed on Feb. 27, 2015.

(51) Int. Cl.
*A61B 17/64* (2006.01)

(52) U.S. Cl.
CPC ...... *A61B 17/6466* (2013.01); *A61B 17/6416* (2013.01); *A61B 17/645* (2013.01)

(58) Field of Classification Search
CPC ............ A61B 17/6475; A61B 17/6483; A61B 17/6458; A61B 17/6416; A61B 17/645; A61B 17/6466; A61B 90/14; A61B 17/8685

See application file for complete search history.

(56) References Cited

U.S. PATENT DOCUMENTS

| | | | |
|---|---|---|---|
| 3,389,734 A | 6/1968 | Gutshall | |
| 4,620,533 A | 11/1986 | Mears | |
| 4,850,746 A | 7/1989 | Finsterwalder et al. | |
| 4,848,368 A | 11/1989 | Kronner | |
| 4,920,959 A | 5/1990 | Witzel et al. | |
| 5,891,144 A | 4/1999 | Mata et al. | |
| 9,131,946 B2 | 9/2015 | Larche et al. | |
| 9,687,278 B2 * | 6/2017 | Childs | A61B 17/7064 |
| 2005/0277936 A1 | 12/2005 | Siravo et al. | |
| 2006/0002784 A1 | 1/2006 | Curtis | |
| 2007/0270956 A1 * | 11/2007 | Heinz | A61F 2/44 623/17.11 |
| 2008/0300630 A1 | 12/2008 | Bonnema et al. | |

(Continued)

FOREIGN PATENT DOCUMENTS

CA 2081466 8/1992
CA 2159295 3/1996

(Continued)

OTHER PUBLICATIONS

International Search Report and Written Opinion dated in PCT/US16/19486, dated Jul. 11, 2016.

*Primary Examiner* — Julianna N Harvey
(74) *Attorney, Agent, or Firm* — Bell & Manning, LLC

(57) ABSTRACT

Devices for the fixation of a bone fracture and methods of using the devices are provided. The devices comprise at least one distal pin assembly configured to engage a first bone fragment, at least one proximal pin assembly configured to engage a second bone fragment, and a pin connector assembly configured to connect the distal and proximal pin assemblies together across the bone fracture.

12 Claims, 17 Drawing Sheets

(56) References Cited

U.S. PATENT DOCUMENTS

| | | |
|---|---|---|
| 2012/0203225 A1 | 8/2012 | Mingozzi et al. |
| 2012/0245704 A1* | 9/2012 | Childs ................ A61B 17/7064 623/23.52 |
| 2013/0317503 A1* | 11/2013 | Songer ................ A61B 17/742 606/66 |
| 2014/0031934 A1* | 1/2014 | Trieu ................ A61F 2/30988 623/17.11 |
| 2014/0277129 A1 | 9/2014 | Arai et al. |
| 2014/0303621 A1 | 10/2014 | Gerold et al. |
| 2014/0364853 A1 | 12/2014 | Mullaney et al. |

FOREIGN PATENT DOCUMENTS

| | | |
|---|---|---|
| CA | 2371670 | 8/2002 |
| CA | 2372713 | 8/2002 |
| CA | 2424020 | 9/2003 |
| CN | 204164141 U | 2/2015 |
| DE | 2607315 | 9/1976 |
| EP | 1839584 | 10/2007 |
| ES | 2126497 | 3/1999 |
| FR | 2674120 | 9/1992 |
| FR | 19910003977 | 9/1992 |
| FR | 2783703 | 3/2000 |
| FR | 2968535 | 6/2012 |
| GB | 8809120 | 5/1988 |
| KR | 20070006596 | 1/2007 |
| WO | WO200205718 | 1/2002 |
| WO | WO2008027375 | 3/2008 |
| WO | WO2010121028 | 10/2010 |
| WO | WO2012040862 | 4/2012 |
| WO | WO2013119812 | 8/2013 |
| ZA | 9904846 | 2/2000 |
| ZA | 9904847 | 2/2000 |

\* cited by examiner

ORTHOPEDIC EXTERNAL FIXATION DEVICE

CROSS-REFERENCE TO RELATED APPLICATION

The present application claims priority to U.S. Provisional Patent Application No. 62/121,904 that was filed on Feb. 27, 2015, the entire contents of which is hereby incorporated by reference.

BACKGROUND

Bone fractures are debilitating injuries that affect millions of people around the world each year. Many of these fractures involve the long bones of the extremities including the femur, tibia, fibula, humerus, radius, and ulna. Fractures to these bones can be particularly painful, difficult to heal, and may require multiple surgeries with months of recovery.

When a patient enters the emergency room with a severe bone fracture, it is often accompanied by many other serious injuries. For instance, bone fractures are a frequent occurrence after a serious car accident, where often times the individual will also have head and respiratory trauma that is of primary concern. Though the critical injuries must be addressed first, once the patient is stable in the emergency department any serious fractures must be stabilized. The patient may need to be transported throughout the emergency department for various imaging and surgical procedures, so it is important to have the injured limb temporarily stabilized to reduce pain and prevent improper healing. Temporary stabilization may be required until the patient and his or her injuries are stable enough for a surgical procedure in the operating room to repair and permanently fixate the fracture. This temporary period can be anywhere from a few hours to a few weeks, depending on the injuries. Once placed, a permanent device may remain affixed for a number of weeks or even months, until the fracture is adequately healed.

There are several forms of temporary fracture stabilization methods including splinting, traction, and external fixation. Splinting may provide support along a fracture until the patient's other critical injuries are stabilized; however, such temporary devices are not always compatible with certain imaging techniques, such as magnetic resonance imaging (MRI), and don't actually fixate the fracture.

Traction is a method for temporary fracture stabilization used in many hospitals and emergency departments. Traction systems separate the two major bone fragments, properly aligning them (reduction) and facilitating proper healing. However, traction is a bulky procedure and can subject the patient to an uncomfortable position without the ability to move for an extended period of time. Bed transfers with this type of fixation are highly impractical, and very difficult to orchestrate.

External fixators have been used for over a century and have two widespread uses: temporary fixation and more permanent applications intended for a longer term treatment (permanent external fixation). Methods for permanent external fixation may utilize multi-pin circular frames and uni-lateral pin-bar systems. Though effective in stabilizing the fracture and keeping the fragments aligned for healing, the installation of these permanent fixation devices can take hours, and the complexity involved with unilateral and pin-point bone screw affixation can be complicated.

Temporary fixation involves the rapid temporary fixation of bone fractures using primarily unilateral pin-bar fixators to provide temporary stability while the patient is stabilized and care is provided during hospitalization. Current temporary fixators employ, at a minimum, four separate pins to achieve fixation. Such devices can take critical time to be applied and pose an increased risk for infection at the exposed sites of pin entry.

SUMMARY

Devices for the fixation of bone fractures are provided. Also provided are methods of using the devices for the fixation of bone fragments. The device comprises at least one distal pin assembly configured to engage a first bone fragment, at least one proximal pin assembly configured to engage a second bone fragment, wherein the second bone fragment is at least partially separated from the first bone fragment by a bone fracture, and a rod-clamp system configured to connect the distal and proximal pin assemblies together to create a bridge across the bone fracture.

Pin assemblies for engaging a bone fragment, orthopedic external fixation devices comprising the pin assemblies, and methods for using the orthopedic external fixation devices to stabilize the bone fragments of a fractured bone are provided.

One embodiment of an orthopedic external fixation device includes: (a) a distal pin assembly configured to engage a first bone fragment; (b) a proximal pin assembly configured to engage a second bone fragment; and (c) a pin assembly connector configured to connect the distal pin assembly to the proximal pin assembly. One embodiment of the distal pin assembly includes: (i) a screw portion having a distal end configured to engage the first bone fragment and a proximal end; and (ii) a support sheath portion having a distal end configured to engage the first bone fragment, a proximal end, and an outer surface, wherein the support sheath portion defines an elongated channel in which the proximal end of the screw portion is disposed. Similarly, one embodiment of the proximal pin assembly comprises: (i) a screw portion having a distal end configured to engage the second bone fragment and a proximal end, and (ii) a support sheath portion having a distal end configured to engage the second bone fragment, a proximal end, and an outer surface, wherein the support sheath portion defines an elongated channel in which the proximal end of the screw portion is disposed. One embodiment of the pin assembly connector comprises: a first clamp; a second clamp; and a connecting rod assembly comprising one or more rods, wherein the first clamp is configured to connect to the outer surface of the support sheath portion of the distal pin assembly and to a rod of the connecting rod assembly; the second clamp is configured to connect to the outer surface of the support sheath portion of the proximal pin assembly and to a rod of the connecting rod assembly.

One embodiment of a method of using the above-described device to stabilize a fractured bone comprising a first bone fragment and a second bone fragment includes the steps of: (a) engaging the first bone fragment with the distal pin assembly; (b) engaging the second bone fragment with the proximal pin assembly; and (c) connecting the distal pin assembly to the proximal pin assembly with the pin assembly connector.

Another embodiment of an orthopedic external fixation device comprises one or more pin assemblies, each configured to engage a bone fragment and comprising: (i) a screw portion having a distal end configured to engage the bone fragment and a proximal end; and (ii) a support sheath portion having a distal end configured to engage the bone fragment; a proximal end; and an outer surface, wherein the support sheath portion defines an elongated channel in which the proximal end of the screw portion is disposed, and further wherein the distal end of the support sheath portion comprises multiple elongated blades running lengthwise along its outer surface, the elongated blades being configured to engage the bone fragment when the pin assembly is in place stabilizing a fractured bone.

One embodiment of an orthopedic external fixation device incorporating the above-described pin assemblies includes: (a) a distal pin assembly configured to engage a first bone fragment; (b) a proximal pin assembly configured to engage a second bone fragment; and (c) a pin assembly connector configured to connect the distal pin assembly to the proximal pin assembly. One embodiment of the distal pin assembly comprises: (i) a screw portion having a distal end configured to engage the first bone fragment and a proximal end; and (ii) a support sheath portion having a distal end configured to engage the first bone fragment; a proximal end; and an outer surface, wherein the support sheath portion defines an elongated channel in which the proximal end of the screw portion is disposed, and further wherein the distal end of the support sheath portion comprises multiple elongated blades running lengthwise along its outer surface, the elongated blades being configured to engage the first bone fragment. One embodiment of the proximal pin assembly comprises: (i) a screw portion having a distal end configured to engage the second bone fragment and a proximal end; and (ii) a support sheath portion having a distal end configured to engage the second bone fragment, wherein the support sheath portion defines an elongated channel in which the proximal end of the screw portion is disposed, and further wherein the distal end of the support sheath portion comprises multiple elongated blades running lengthwise along its outer surface, the elongated blades being configured to engage the second bone fragment.

One embodiment of a method of using the above-described device to stabilize a fractured bone comprising a first bone fragment and a second bone fragment includes the steps of: (a) engaging the first bone fragment with the distal pin assembly; (b) engaging the second bone fragment with the proximal pin assembly; and (c) connecting the distal pin assembly to the proximal pin assembly with the pin assembly connector.

Other principal features and advantages of the invention will become apparent to those skilled in the art upon review of the following drawings, the detailed description, and the appended claims.

BRIEF DESCRIPTION OF THE DRAWINGS

Illustrative embodiments of the invention will hereafter be described with reference to the accompanying drawings, wherein like numerals denote like elements.

DETAILED DESCRIPTION

The following description of the embodiments of the devices and methods is merely illustrative and is not intended to limit the invention to a specific embodiment or its use to a specific application.

The terms "distal end" and "proximal end" are used throughout this disclosure in reference to the screw portion, the support sheath portion and the cap portion of each pin assembly. As used herein the "distal end" refers to the end of the component that is nearest the bone fragment when the pin assembly is in place and the "proximal end" refers to the end of the component that is disposed opposite, or substantially opposite, the distal end.

Figure 1:
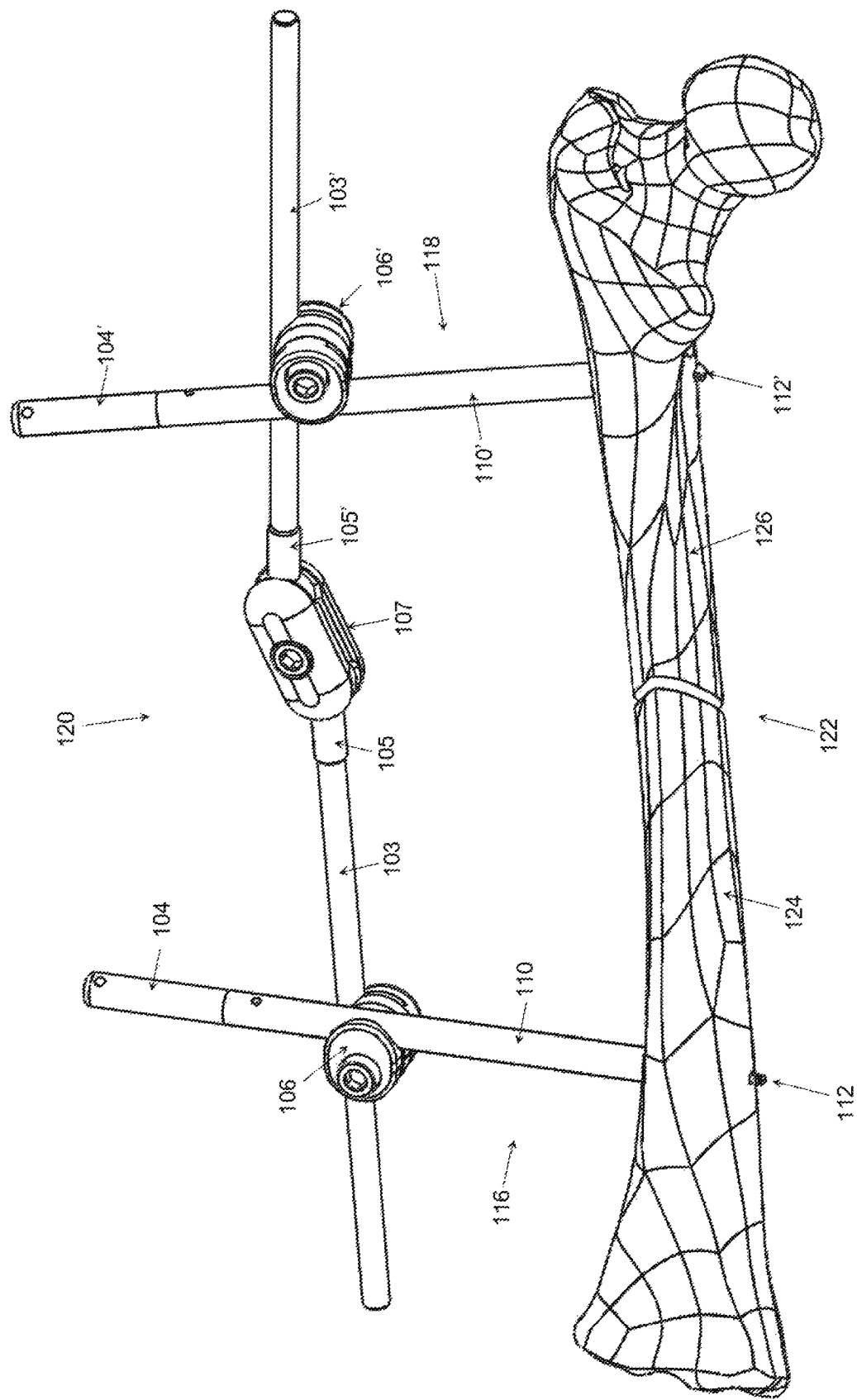
FIG. 1 shows a perspective view of an embodiment of an external fixation device fixated to a fractured bone.
Figure 4:
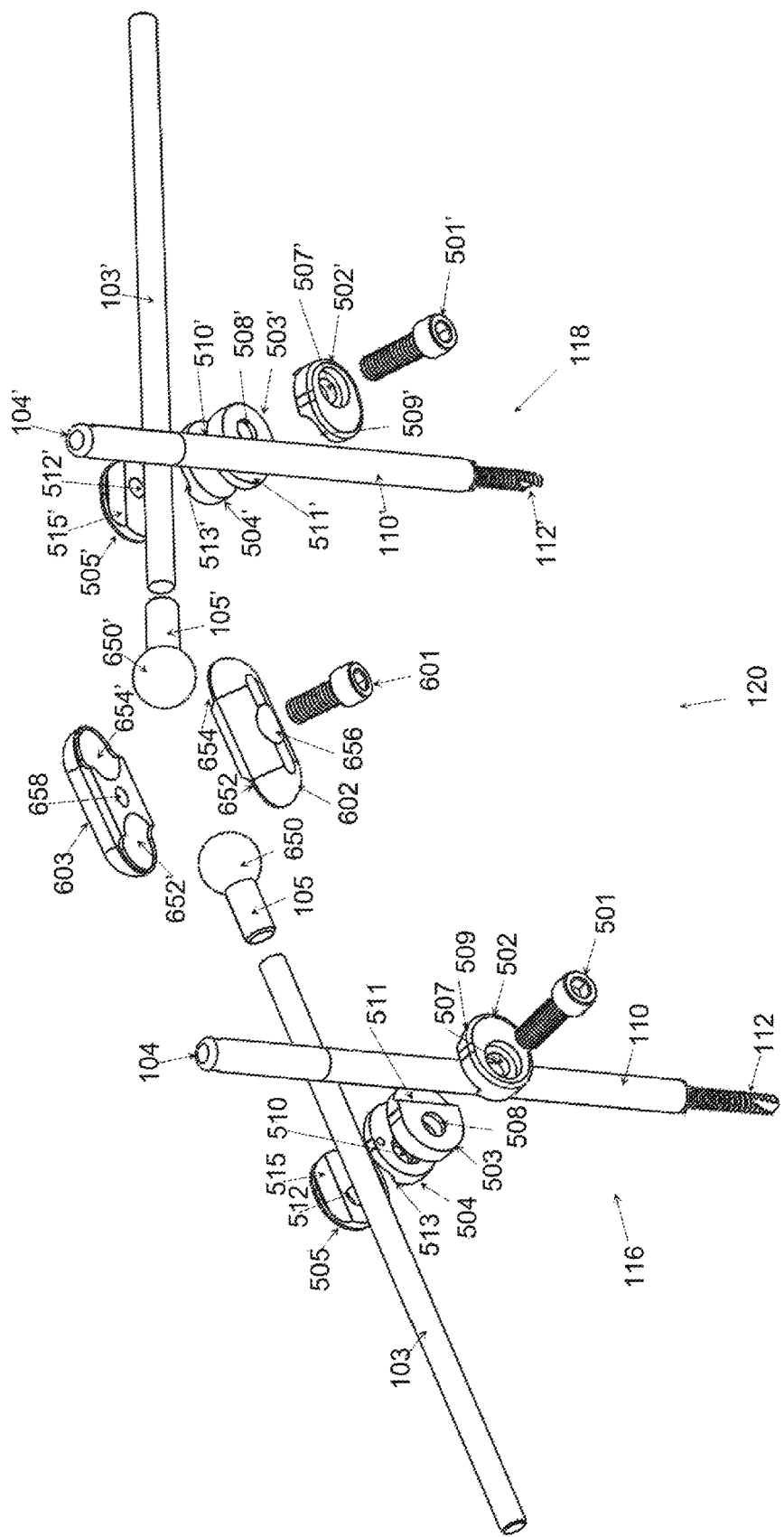
FIG. 4 shows an exploded perspective view of an embodiment of an external fixation device.
Figure 5:
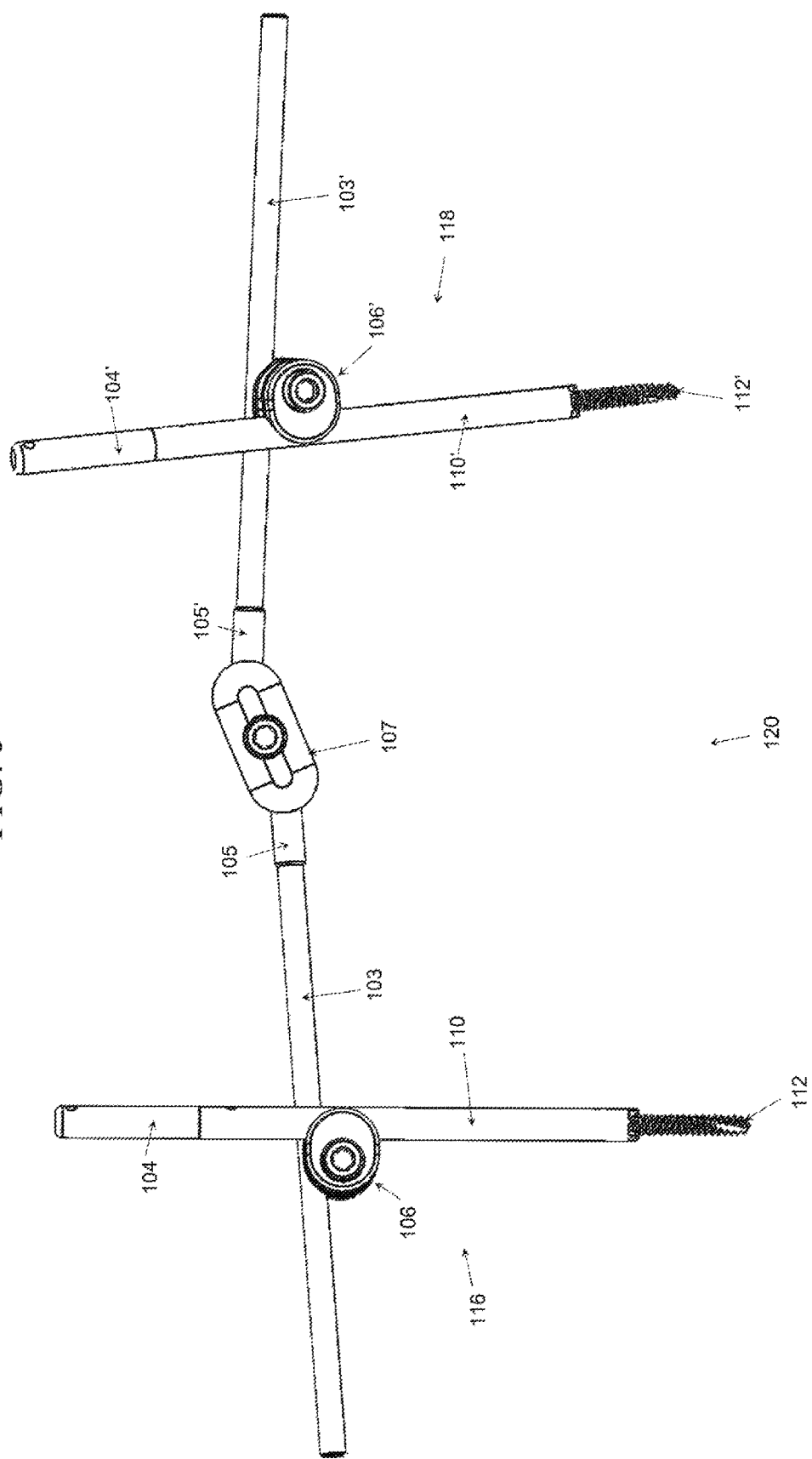
FIG. 5 shows a front view of an embodiment of an external fixation device.
Figure 7:
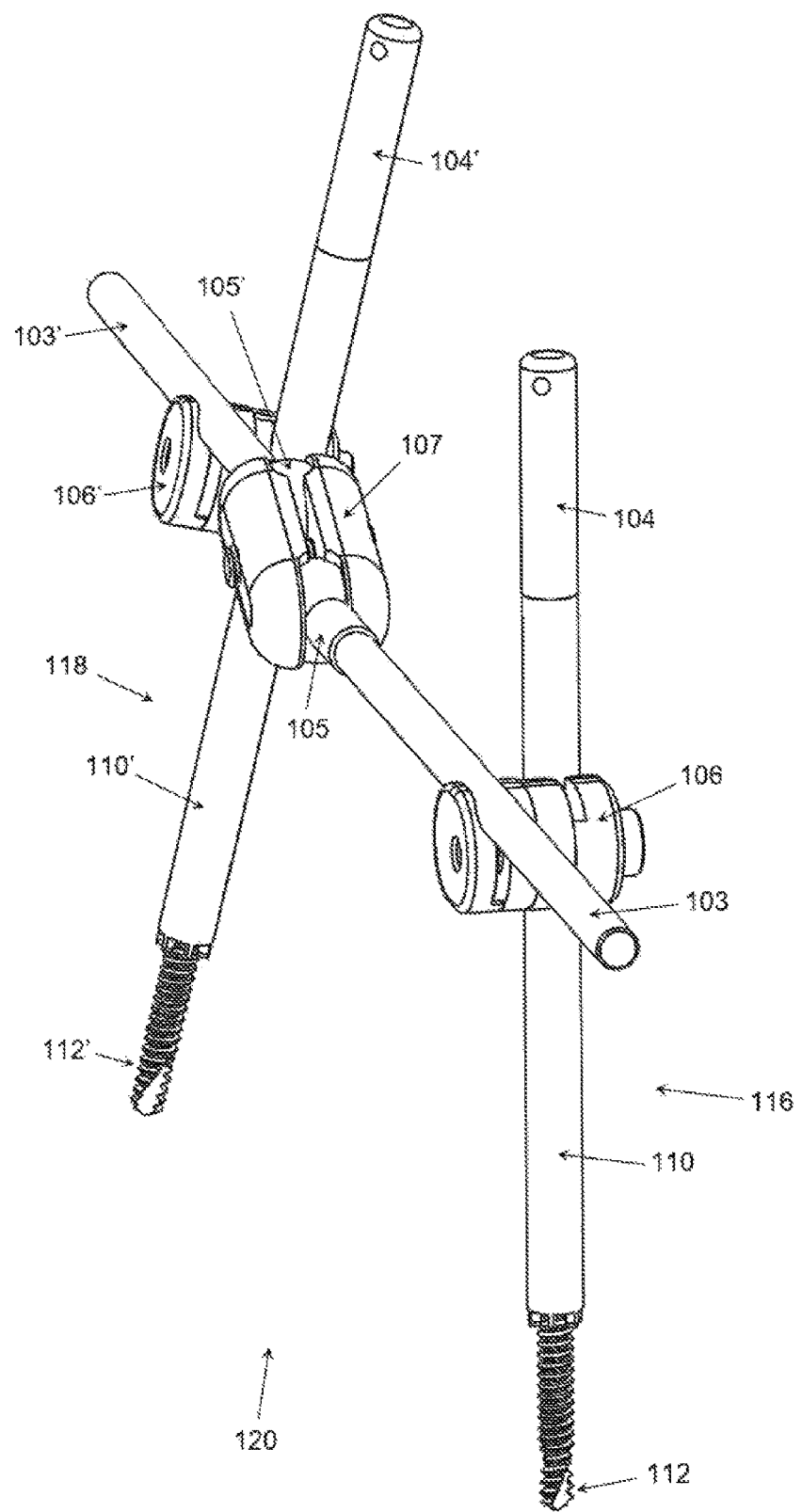
FIG. 7 shows a side view of an embodiment of an external fixation device.

One embodiment of an orthopedic external fixation device 120 is shown in FIG. 1, FIG. 4, FIG. 5, and FIG. 7. FIG. 5 and FIG. 7 show orthopedic external fixation device 120 alone. FIG. 4 is an exploded view of the orthopedic external fixation device 120. FIG. 1 shows orthopedic external fixation device 120 in combination with fractured bone 122. The orthopedic external fixation device 120 includes distal pin assembly 116 configured to engage with first bone fragment 124; proximal pin assembly 118 configured to engage with second bone fragment 126; first rod 103 connecting first connector clamp 106 to center clamp 107; and second rod 103' connecting second connector clamp 106' to center clamp 107. First and second rods 103, 103' may be solid or hollow and need not have a circular cross-section. The connections between first and second rods 103, 103' and center clamp 107 may be ball-and-socket type connections, as shown in FIG. 4. For example, as shown in FIG. 4 and discussed in more detail below, a first ball-and-socket connection is formed between a spherical surface (i.e., a "ball") 650 at an end of first rod 103 and a mating spherical cavity defined in one end of center clamp 107 and a second ball-and-socket connection is formed between a spherical surface (i.e., a "ball") 650' at an end of second rod 103' and a mating spherical cavity defined in an opposing end of center clamp 107. Spherical surfaces 650, 650' can be an integral part of the end of the rods, or can be part of an end piece 105, 105' fitted on the end of a rod, as shown in FIG. 4.

The rod-clamp connections provide a pin assembly connector that is configured to connect distal pin assembly 116 to proximal pin assembly 118. Distal pin assembly 116 comprises cap portion 104 attached to the proximal end 160 of screw portion 112. Proximal pin assembly 118 also comprises a cap portion 104' attached to the proximal end 160 of screw portion 112'. Cap portions 104, 104' are configured such that, when their respective pin assemblies 116, 118 are engaged with their respective bone fragments 124, 126 and cap portions 104, 104' are tightened onto the proximal ends of their respective screw portions 112, 112', the distal ends of the cap portions engage with (e.g., press against) the proximal ends of their respective support sheath portions 110, 110', thereby exerting a compressive force on said support sheath portions.

As shown in this embodiment, each support sheath portion has a distal end configured to engage a bone fragment, wherein the support sheath portion defines an elongated channel in which the proximal end of a screw portion is disposed and out of which the distal end of the screw portion extends. For example, the support sheath portion may comprise a distal end, an oppositely disposed proximal end and a body (e.g., a hollow shaft) connecting the distal and proximal ends, wherein the elongated channel extends through the body from the distal end to the proximal end. The engagement between a bone fragment and the distal end of the support sheath portion may be provided, for example, by extensions 701 (e.g., tines) extending outwardly from the leading edge 702 of the distal end of the support sheath portion that are configured to anchor the support sheath portion to a bone fragment and hold the support sheath portion in a given position and alignment along the bone fragment. The support sheath portion fits over the screw portion to allow the support sheath portion to slide over the proximal end of the screw portion and engage the bone fragment.

In the present embodiment, as best seen in FIG. 4, connector clamps 106, 106' can be seen to be comprised of compression screws 501, 501'; outer sheath clamp plates 502, 502'; inner sheath clamp plates 503, 503'; inner rod clamp plates 504, 504'; and outer rod clamp plate 505, 505'. Clamp plates 502, 503, and 504 each define a bore hole 507, 508, and 510 through which compression screw 501 can be placed, and clamp plate 505 defines a tapped bore hole (i.e., a threaded screw hole) 512 into which compression screw 501 can be screwed. Similarly, clamp plates 502', 503', and 504' each define a bore hole 507', 508', 510' through which compression screw 501' can be inserted, and clamp plate 505' defines a tapped bore hole (i.e., a threaded screw hole) 512' into which compression screw 501' can be screwed. Outer sheath clamp plate 502 and inner sheath clamp plate 503 clamp support sheath portion 110 between them to provide a clamping grip on an outer surface (e.g., the circumference) of support sheath portion 110 when compression screw 501 is tightened. Similarly, outer sheath clamp plate 502' and inner sheath clamp plate 503' clamp support sheath portion 110' between them to provide a clamping grip on an outer surface (e.g., the circumference) of support sheath portion 110' when compression screw 501' is tightened. Inner rod clamp plate 504 and outer rod clamp plate 505 provide a clamping grip on rod 103 when compression screw 501 is tightened. Similarly, inner rod clamp plate 504' and outer rod clamp plate 505' provide a clamping grip on rod 103' when compression screw 501' is tightened. The effective result is a clamping grip between pin assembly 116 and rod 103 and a clamping grip between pin assembly 118 and rod 103'.

The inner surfaces of the clamp plates (i.e., the surfaces that make contact with a support sheath portion or a rod) may be contoured to match the contour of the outer surface of the support sheath portion or rod, as illustrated by grooves 509, 509', 511, 511', 513, 513', 515, and 515'. In addition, inner sheath plate 503 and inner rod plate 504 need not be separate pieces, but can be a single integral piece, such that one face of the piece provides the inner sheath plate and the opposing face provides the inner rod plate.

In the present embodiment, as best seen in FIG. 4, center clamp 107 can be seen to be comprised of compression screw 601; upper center clamp 602; and lower center clamp 603. Upper center clamp 602 defines a bore hole 656 through which compression screw 601 can be inserted and lower center clamp 603 defines a tapped bore hole (i.e., a threaded screw hole) 658 into which compression screw 601 can be screwed. Hemispherical cavities 652, 654, 652', and 654' are defined in the opposing ends of both the upper and lower center clamps 602 and 603. When compression screw 601 is inserted through the screw holes 656 and 658 in upper and lower center clamps 602 and 603 and tightened, hemispherical cavities 652 and 652' come together to form a spherical cavity that provides a clamping force on spherical surface 650 and hemispherical cavities 654 and 654' come together to form a spherical cavity that provides a clamping force on spherical surface 650'. The effective result is ball-and-socket joint between center clamp 107 and rod 103 and a ball-and-socket joint between center clamp 107 and rod 103'.

Figure 9:
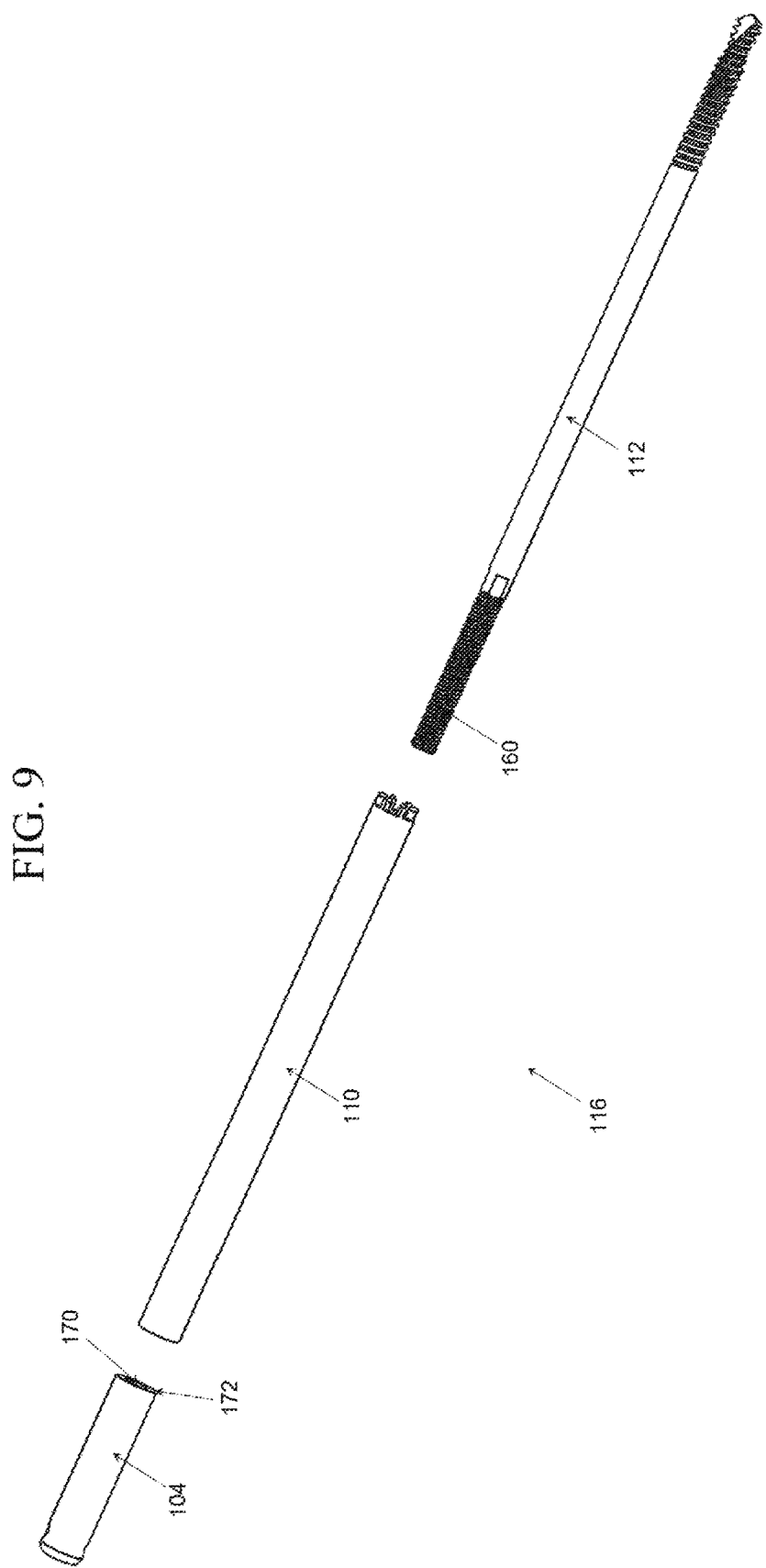
FIG. 9 shows an exploded perspective view of an embodiment of a pin assembly for an external fixation device.

In the presented embodiment, as best seen in FIG. 9, the distal end of cap portion 104 defines a bore hole 170, the inner surface of which comprises internal screw threads configured to engage with the threaded proximal end 160 of screw portion 112. The distal end of cap portion 104 further comprises a surface 172 configured to engage with the proximal end of support sheath portion 110 and provide compression onto support sheath portion 110 when cap portion 104 is tightened onto screw portion 112. Cap portion 104 can engage with support sheath portion 110 simply by pressing against it. Cap portion 104 further comprises a proximal end disposed opposite its distal end and a body, such as a hollow shaft, extending between the proximal and distal ends. Support sheath portion 110 of distal pin assembly 116 slides over screw portion 112, such that the distal end of screw portion 112 extends out of the distal end of support sheath portion 110.

Figure 11:
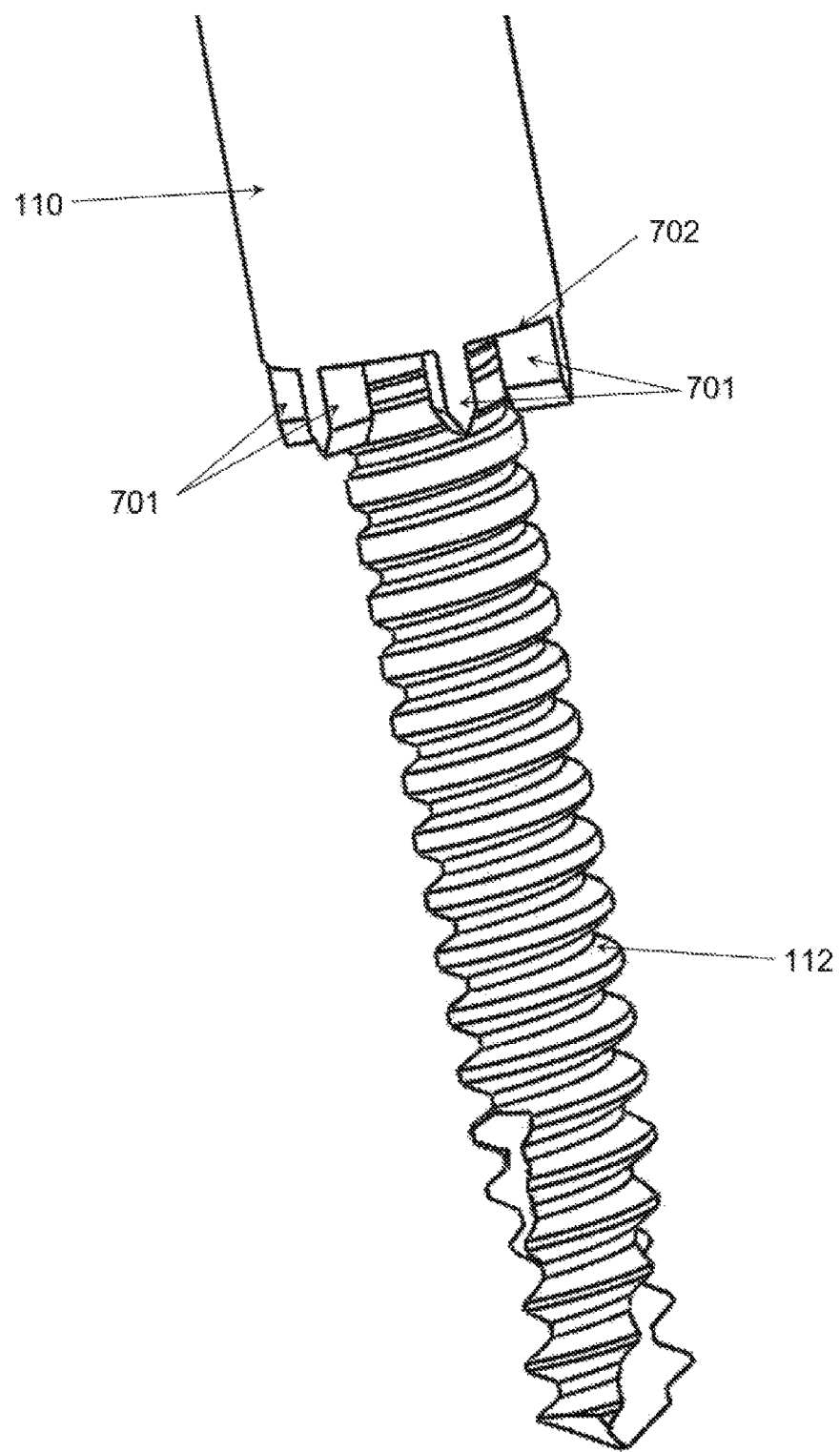
FIG. 11 shows a close-up view of an embodiment of the pin assembly including multiple sharp extension (tine) features.
Figure 16:
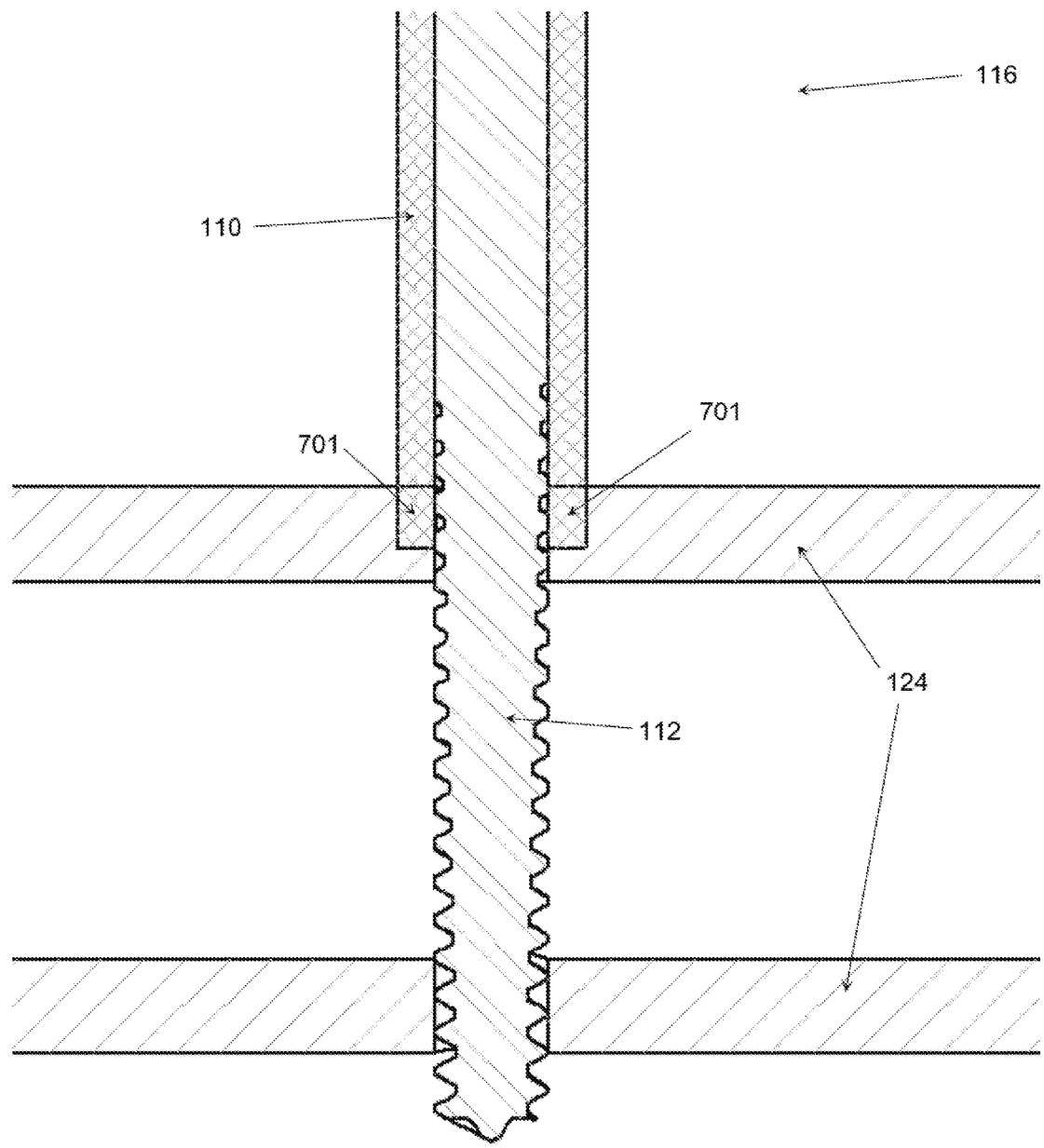
FIG. 16 shows a cross-section view of an embodiment of the pin assembly affixed to a fractured portion of bone, including multiple sharp extension (tine) features.

FIG. 11 shows only the distal end of distal pin assembly 116 in the presented embodiment. Support sheath portion 110 has a distal end configured with multiple sharp extensions 701 (e.g. tines) protruding from leading edge 702 meant to engage bone fragment 124. FIG. 16 shows a cross-section view of the distal pin assembly 116 installed in bone fragment 124. As shown in this figure, a threaded section at the tip of the distal end of screw portion 112 extends out of the distal end of support sheath portion 110 and is engaged with bone fragment 124 via extensions 701.

Although only the distal pin assembly and the first bone fragment are shown in FIGS. 9, 11, and 16, the proximal pin assembly and second bone fragment can have equivalent components and configurations. Similarly, although only the distal pin assembly and the first bone fragment are shown in FIGS. 10, 12-15, and 17 (described below), the proximal pin assembly and second bone fragment can have equivalent components and configurations.

Figure 2:
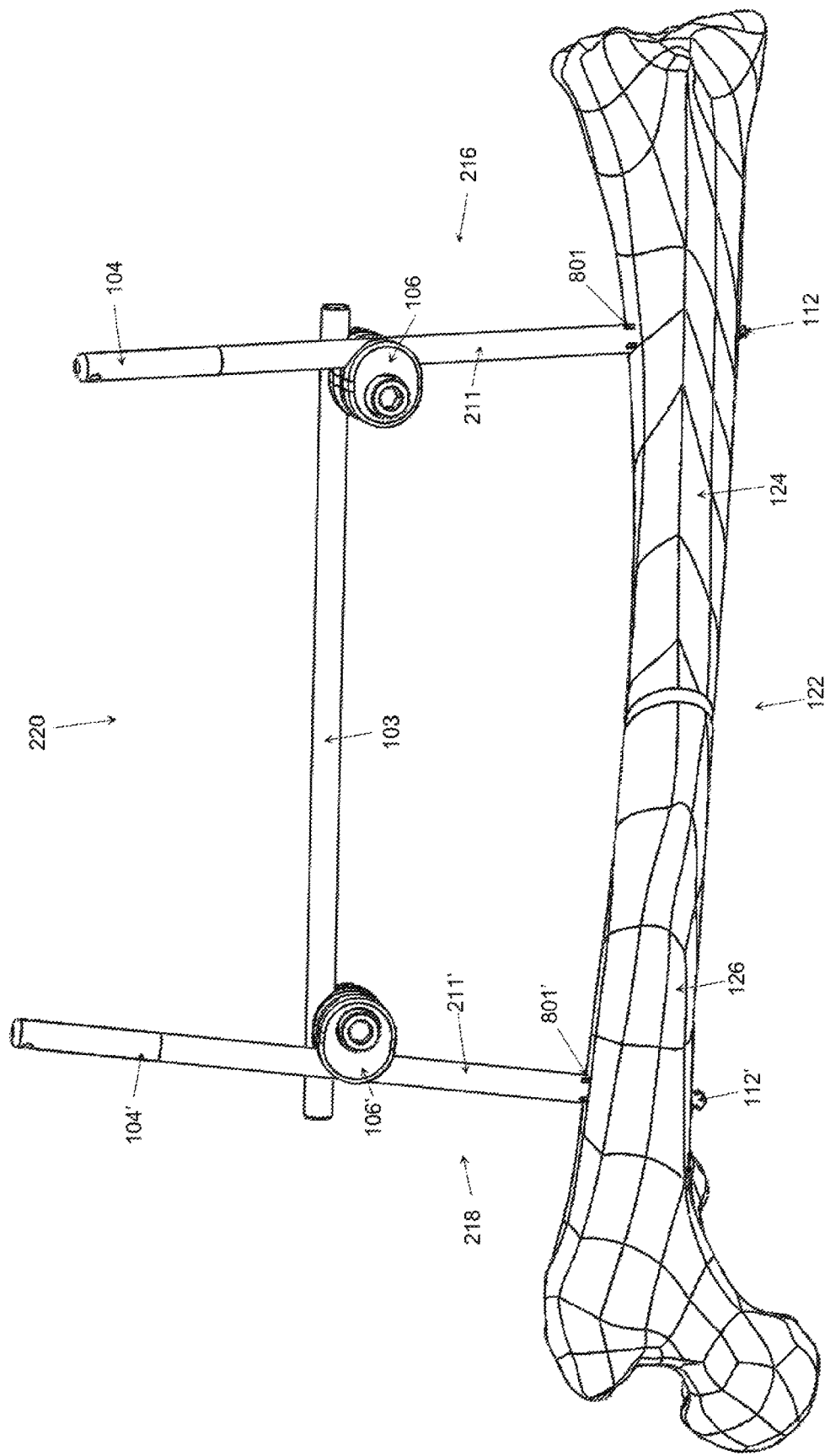
FIG. 2 shows a perspective view of an embodiment of an external fixation device fixated to a fractured bone.
Figure 6:
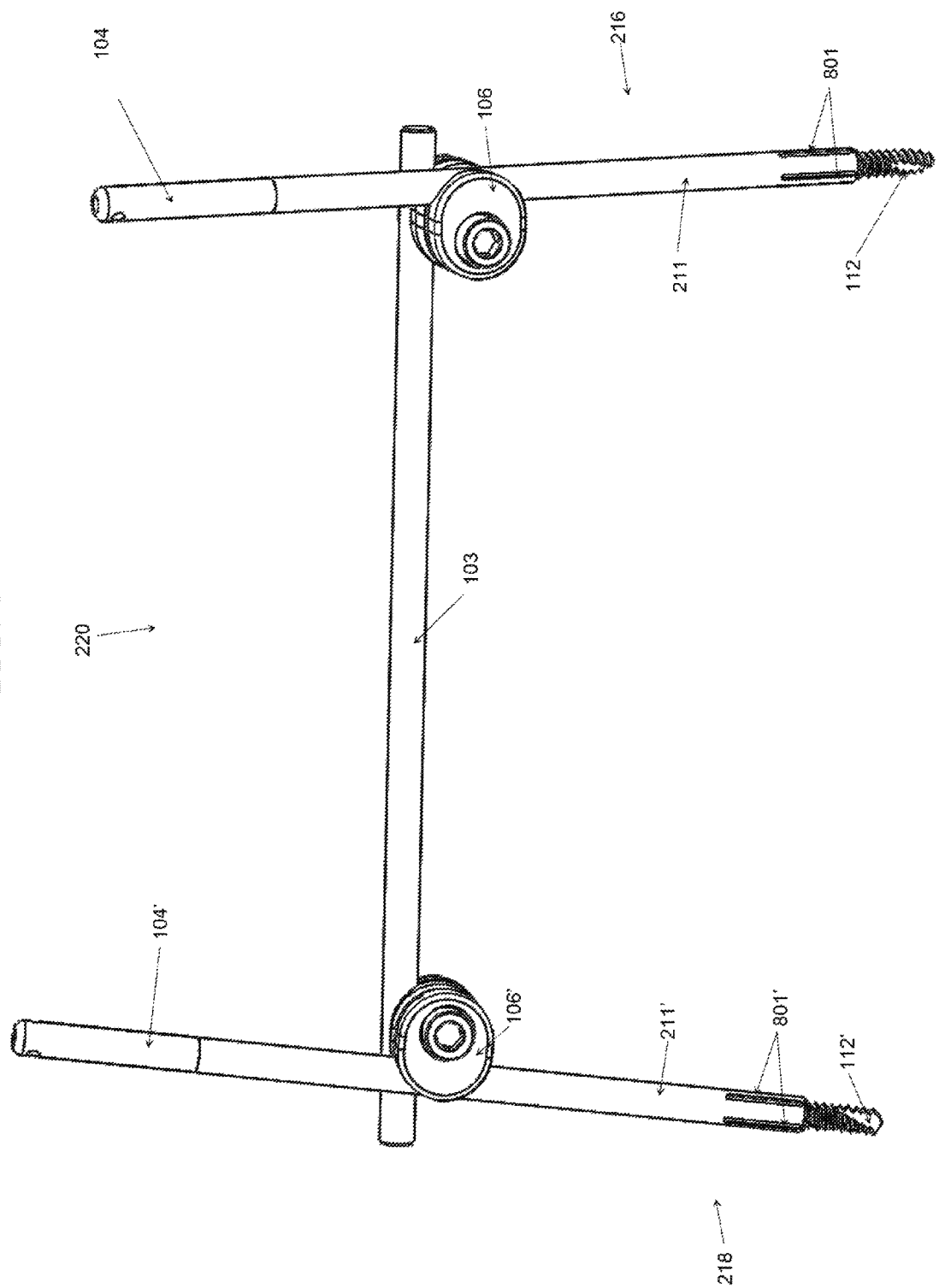
FIG. 6 shows a front view of an embodiment of an external fixation device.
Figure 8:
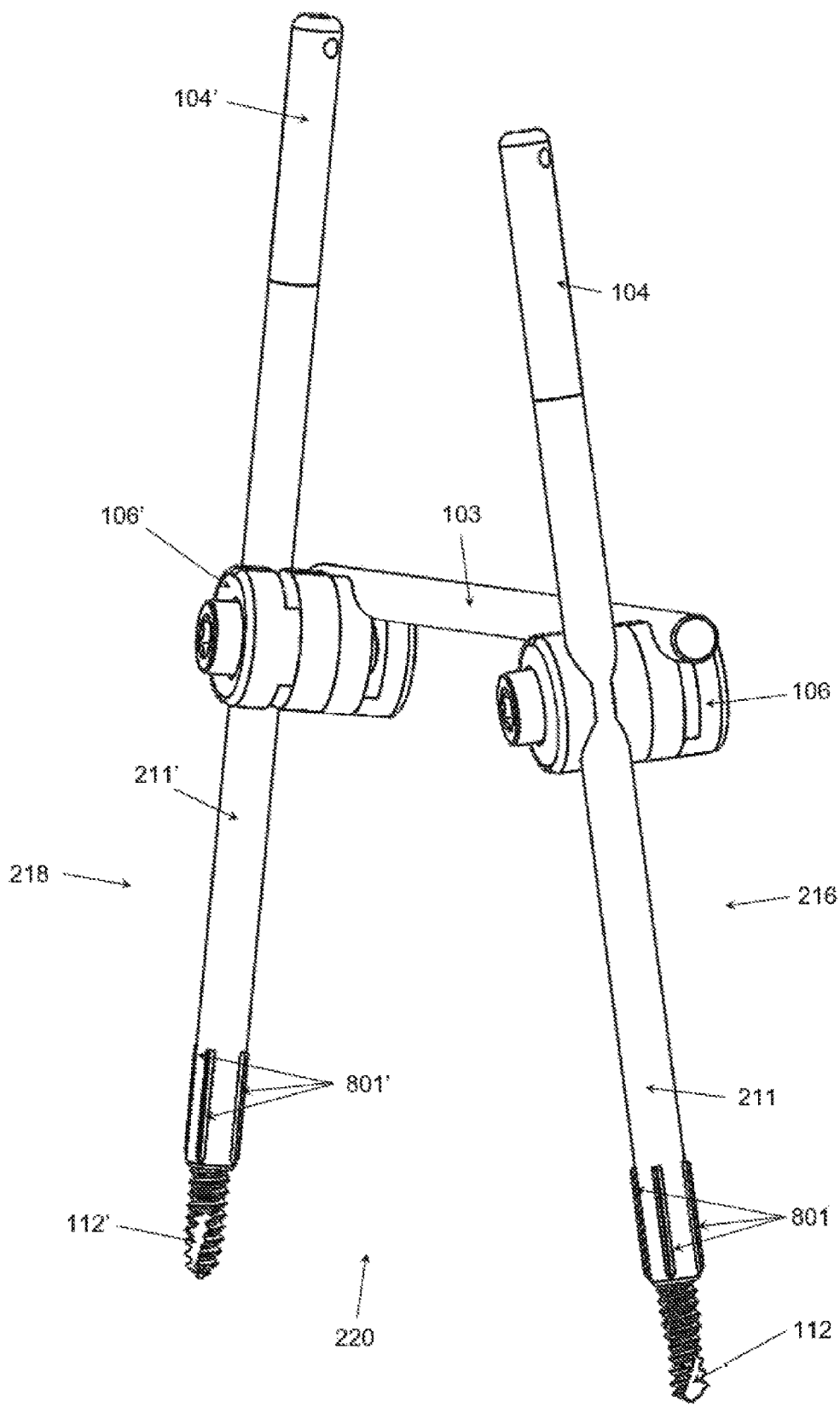
FIG. 8 shows a side view of an embodiment of an external fixation device.

Another embodiment of an orthopedic external fixation device 220 is shown in FIG. 2, FIG. 6, and FIG. 8. FIG. 6 and FIG. 8 show the orthopedic external fixation device alone. FIG. 2 shows orthopedic external fixation device 220 in combination with fractured bone 122. This embodiment of the orthopedic external fixation device uses the same cap portions 104, 104', connector clamps 106, 106', and screw portions 112, 112' as the device of FIG. 1, but uses only one rod 103 to connect connector clamps 106, 106'. In addition, the support sheath portions 211, 211' in this embodiment of the device have a bladed configuration at their distal ends, as discussed in greater detail below. The orthopedic external fixation device 220 includes distal pin assembly 216 configured to engage with first bone fragment 124; proximal pin assembly 218 configured to engage with second bone fragment 126; and rod 103 connected to first connector clamp 106 and to second connector clamp 106', such that it bridges the first and second connector clamps. More specifically, a first end of rod 103 is clamped between inner rod clamp plate 504 and outer rod clamp plate 505 and a second end of rod 103 is clamped between inner rod clamp plate 504' and outer rod clamp plate 505'.

Figure 10:
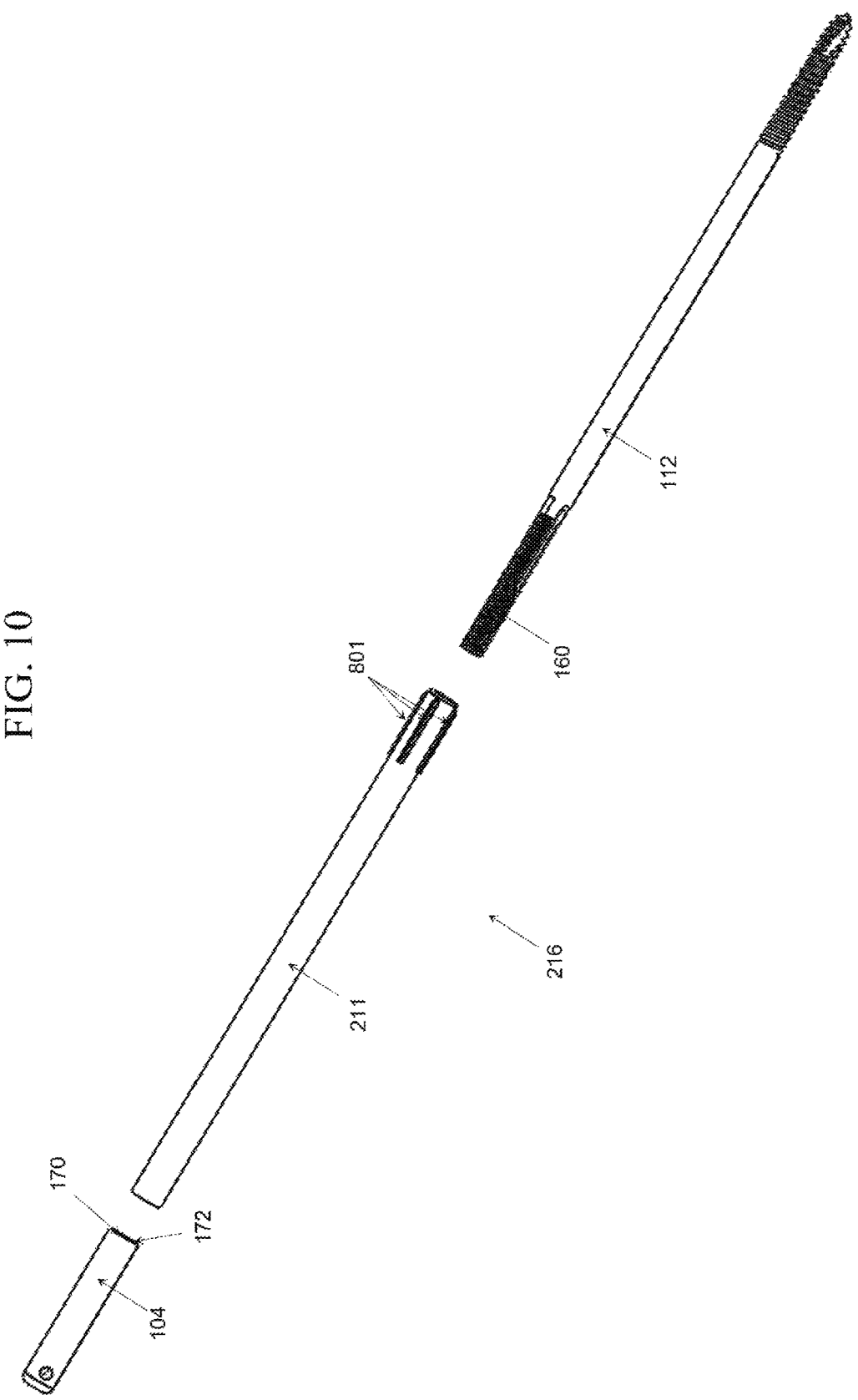
FIG. 10 shows an exploded perspective view of an embodiment of a pin assembly for an external fixation device.

The rod-clamp connections are configured to connect distal pin assembly 216 to proximal pin assembly 218. Distal pin assembly 216 comprises cap portion 104 attached to the proximal end of screw portion 112. Proximal pin assembly 218 also comprises a cap portion 104' attached to the proximal end of its screw portion 112'. The structure of the screw portion, illustrated in FIG. 10, is the same as that of the screw portion shown in FIG. 9. As in the embodiment of the external fixation device depicted in FIG. 1, cap portions 104, 104' are configured such that, when their respective pin assemblies 216, 218 are engaged with their respective bone fragments 124, 126 and cap portions 104, 104' are tightened onto the proximal ends of their respective screw portions, the distal ends of the cap portions engage with (e.g., press against) the proximal ends of their respective support sheath portions 211, 211', thereby exerting a compressive force on said support sheath portions.

As in the device shown in FIG. 1, the orthopedic external fixation device of FIGS. 2, 6, and 8 comprises pin assemblies, each of which includes a support sheath portion having a distal end configured to engage a bone fragment, wherein the support sheath portion defines an elongated channel in which the proximal end of a screw portion is disposed and out of which the distal end of the screw portion extends. For example, the support sheath portion may comprise a distal end, an oppositely disposed proximal end and a body (e.g., a hollow shaft) connecting the distal and proximal ends, wherein the elongated channel extends through the body from the distal end to the proximal end. However, the alternative embodiments of support sheath portions 211, 211' shown in FIGS. 2, 6, and 8 include a plurality (for example, at least two, at least three, or at least four) of blades 801, 801' running lengthwise along an outer surface of the distal end of the support sheath portions. In this embodiment, the blades have a parallel, or substantially parallel, arrangement with each other and with the longitudinal axes of the support sheath portions. The engagement between a bone fragment and the distal end of the bladed support sheath portion may be provided, for example, by blades 801, 801', each of which has a sharp leading edge 821 (or "point"), as seen in FIGS. 12, 13, 14, 15, and 17, and is configured to be inserted into a bone fragment in order to anchor the support sheath portion to said bone fragment and hold the support sheath portion in a given position along the bone fragment. As illustrated in this embodiment, the sharp leading edges 821 of the blades may terminate at the leading edge of the support sheath portion.

In the presented embodiment, as best seen in FIG. 10, the distal end of cap portion 104 defines a bore hole 170, the inner surface of which comprises internal screw threads configured to engage with the threaded proximal end 160 of screw portion 112. The distal end of cap portion 104 further comprises a surface 172 configured to engage with the proximal end of bladed support sheath portion 211 and provide compression onto bladed support sheath portion 211 when cap portion 104 is tightened onto screw portion 112. Cap portion 104 can engage with bladed support sheath portion 211 simply by pressing against it. Cap portion 104 further comprises a proximal end disposed opposite its distal end and a body, such as a hollow shaft, extending between the proximal and distal ends. Bladed support sheath portion 211 of distal pin assembly 216 slides over screw portion 112, such that the distal end of screw portion 112 extends out of the distal end of bladed support sheath portion 211.

Figure 12:
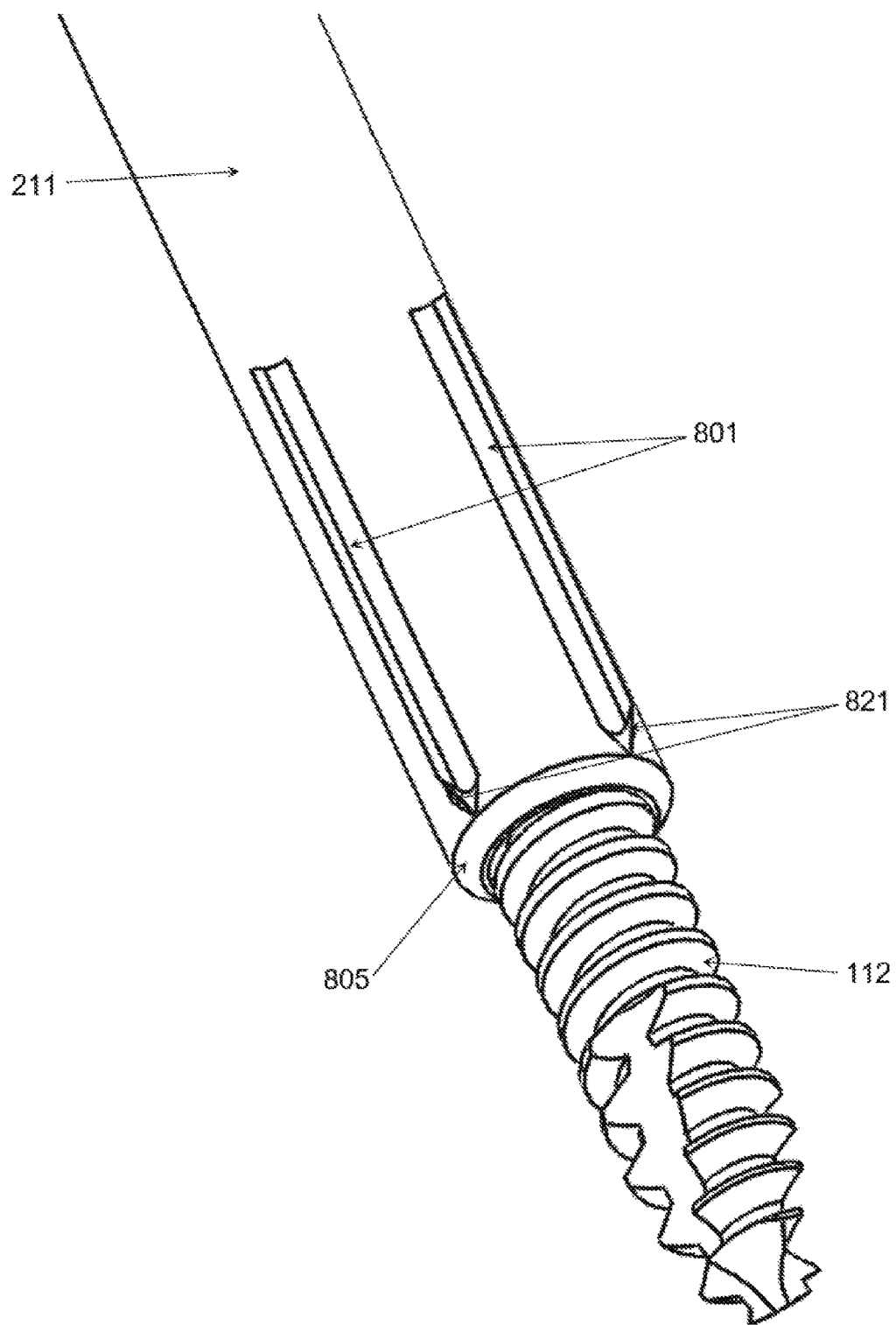
FIG. 12 shows a close-up view of an embodiment of the pin assembly including multiple sharp elongated blade features.
Figure 17:
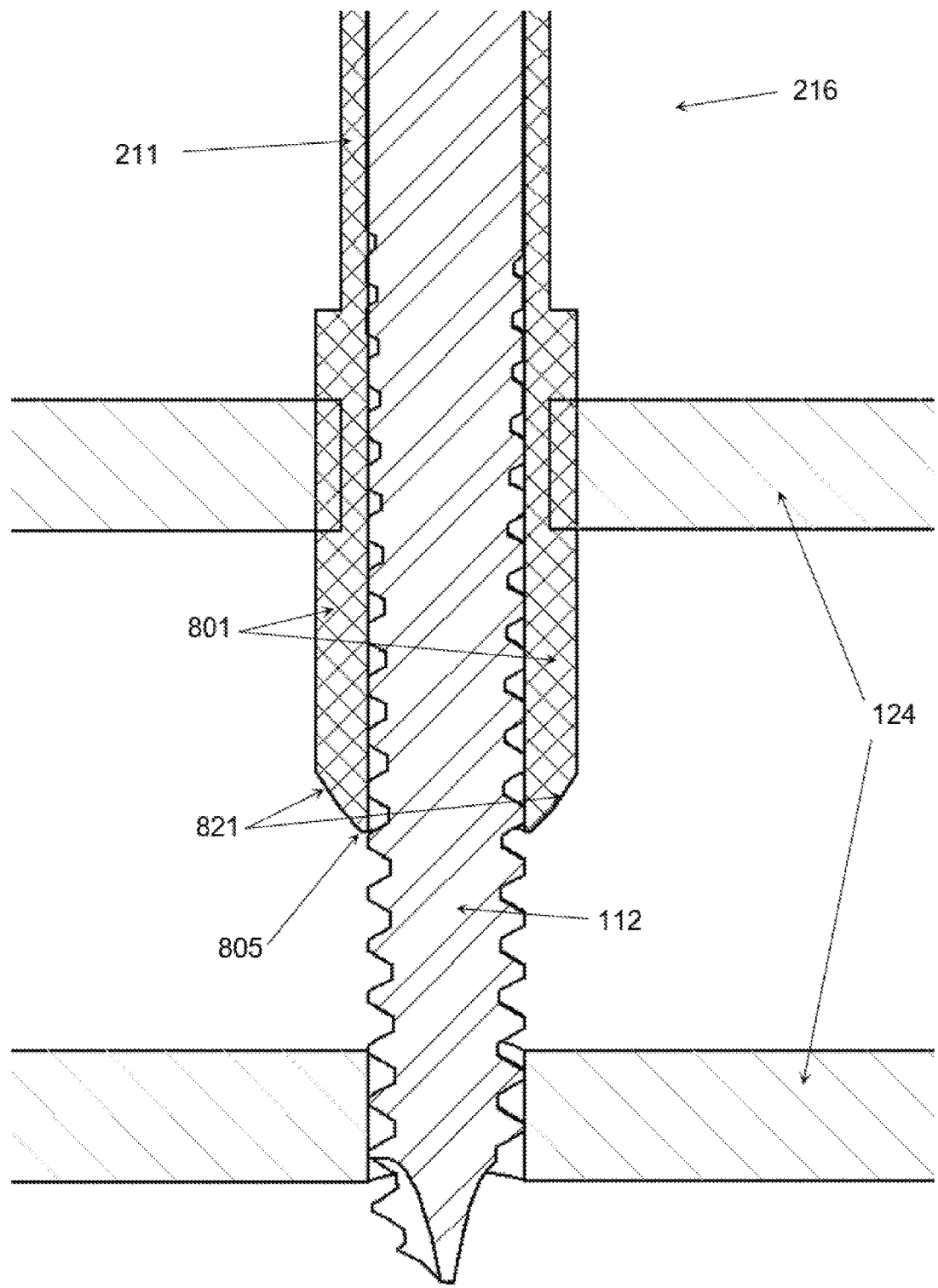
FIG. 17 shows a cross-section view of an embodiment of the pin assembly affixed to a fractured portion of bone, including multiple sharp elongated blade features.

FIG. 12 shows only the distal end of a pin assembly in the presented embodiment. As discussed above, bladed support sheath portion 211 has a distal end configured with multiple sharp elongated blades 801 arranged around the circumference of its outer surface. The blades are configured to (i.e., designed to) penetrate bone fragment 124 when the orthopedic external fixation device is stabilizing fractured bone 122. This penetration can be facilitated by the sharp leading edges 821 at the distal end of each blade 801. In addition, the blades may have a triangular cross-section with an upward facing point in order to facilitate their insertion into a bone fragment. Optionally, the faces of the triangular blades may be hollow ground, as illustrated in FIG. 12. The triangular blades with hollow ground faces are considered to fall within the category of blades having a triangular cross-section for the purposes of this disclosure. FIG. 17 shows a cross-sectional view of the pin assembly of the presented embodiment installed in bone fragment 124. As illustrated in this view, blades 801 extend at least partially through the width of the bone fragment when the device is stabilizing the bone. Screw portion 112 is also engaged in bone fragment 124 and is disposed within bladed support sheath portion 211. The leading edge 805 of the distal end of bladed support sheath portion 211 may be tapered so that the outer diameter at the tip of the support sheath portion is only slightly larger than the diameter of the bore hole formed by the threaded end of screw portion 112 as it is installed into bone fragment 124. This facilitates the insertion of leading edge 805 into bone fragment 124.

Figure 13:
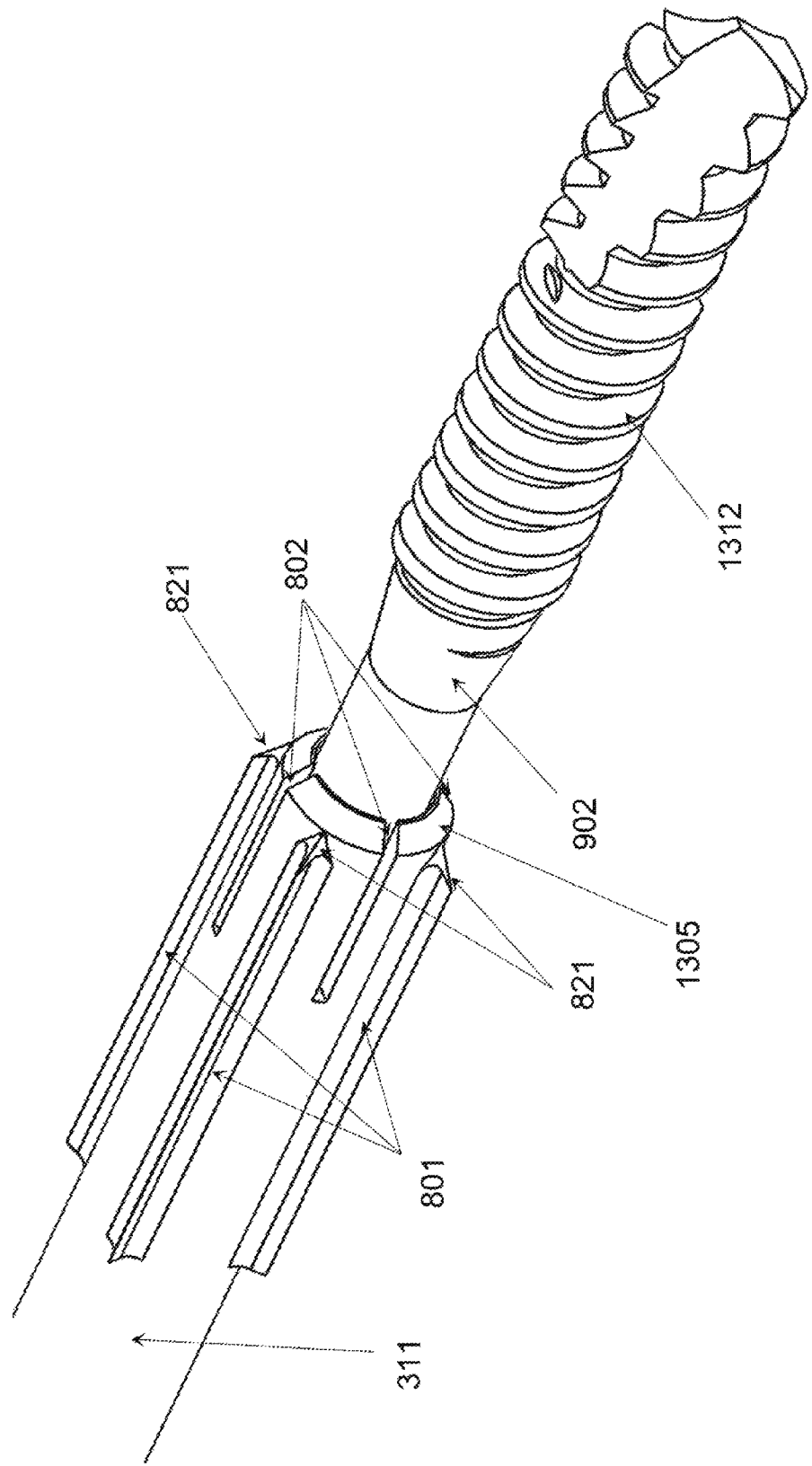
FIG. 13 shows a close-up view of an embodiment of the pin assembly including multiple sharp elongated blade features, expansion slots, and a threaded section of the screw with a conical section above it.

FIG. 13 shows only the distal end of a pin assembly in an additional embodiment. Like the support sheath portion shown in FIG. 12, the support sheath portion 311 in this embodiment has a distal end configured with multiple sharp elongated blades 801 arranged around the circumference of its outer surface. Bladed support sheath portion 311 further includes multiple elongated expansion slots 802 extending into its distal end from its leading edge. The elongated slots are configured to allow the distal end of the support sheath portion to expand outwardly when the support sheath portion is passed over the screw portion to engage bone fragment 124. This design makes it possible for the threaded section of the screw portion to have a diameter that is the same as, or larger than, the diameter of the slotted section at the distal end of the support sheath portion. As a result, the bore hole created in bone fragment 124 by the threaded section of screw portion 1312 can have a diameter that is the same or larger than the outer diameter of the slotted section of support sheath portion 311 (for the purposes of this description, the blades are not taken into account when determining the outer diameter of the slotted section of the support sheath portion). This facilitates the insertion of the distal end of support sheath portion 311 into bone fragment 124. Screw portion 1312 may also include a conical section 902 above its threaded section. Conical section 902 is tapered toward support sheath portion 311 and configured to force the expansion of the distal end of the support sheath portion 311. In addition, as shown in FIG. 13, the leading edge 1305 of bladed support sheath portion 311 can also be tapered to further facilitate the insertion of the support sheath portion into bone fragment 124.

Figure 14:
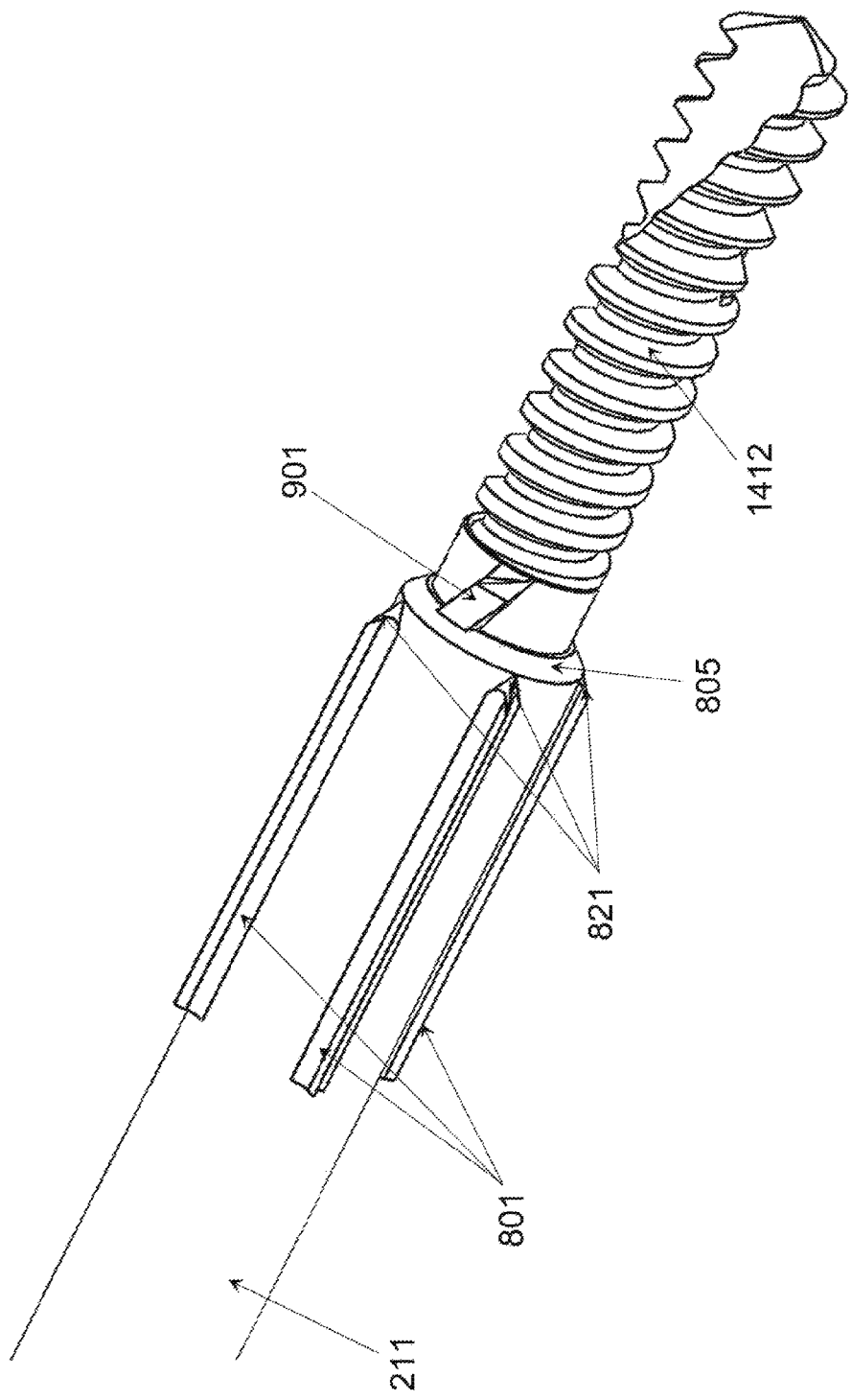
FIG. 14 shows a close-up view of an embodiment of the pin assembly including multiple sharp elongated blade features and a threaded section of the screw with a cutting section above it.

FIG. 14 shows only the distal end of a pin assembly in an additional embodiment. Here, again, bladed support sheath portion 211 has a distal end configured with multiple sharp elongated blades 801 arranged around the circumference of its outer surface. In this embodiment, screw portion 1412 includes a cutting section comprising one or multiple cutting edges 901 extending outwardly from its circumference above the threaded section, wherein cutting edge(s) 901 are configured to engage and bore a hole through the outer portion of bone fragment 124 as screw portion 1412 is installed into bone fragment 124. Tapered front edge 805 of bladed support sheath portion 211 can then be inserted into the resulting bore hole.

Figure 15:
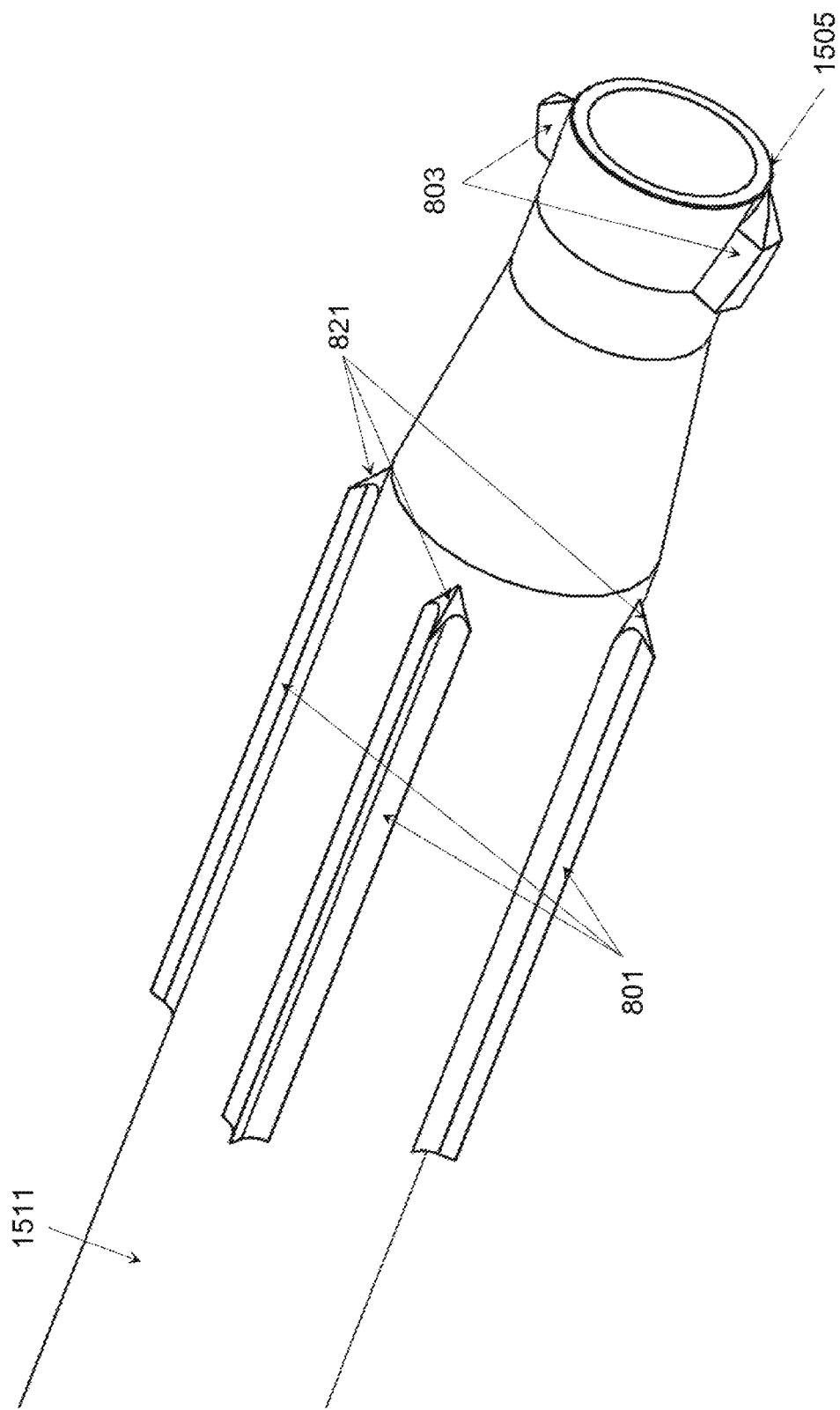
FIG. 15 shows a close-up view of an embodiment of the support sheath including multiple sharp elongated blade features and cutting edges, wherein the bladed section and the cutting section are separated by a tapered, conical section.

FIG. 15 shows only the distal end of a bladed support sheath portion 1511 in an additional embodiment. As in previous embodiments, support sheath portion 1511 has a distal end configured with multiple sharp elongated blades 801 arranged around the circumference of its outer surface. The leading edge 1505 of the distal end of bladed support sheath portion 1511 is flanked by multiple cutting edges 803 around its circumference. Cutting edges 803 are configured to engage and bore a hole through the outer portion of bone fragment 124 when the cutting section is drilled into the bone fragment. The trailing part of support sheath portion 1511 can then follow leading edge 1505 into the resulting bore hole.

Figure 3:
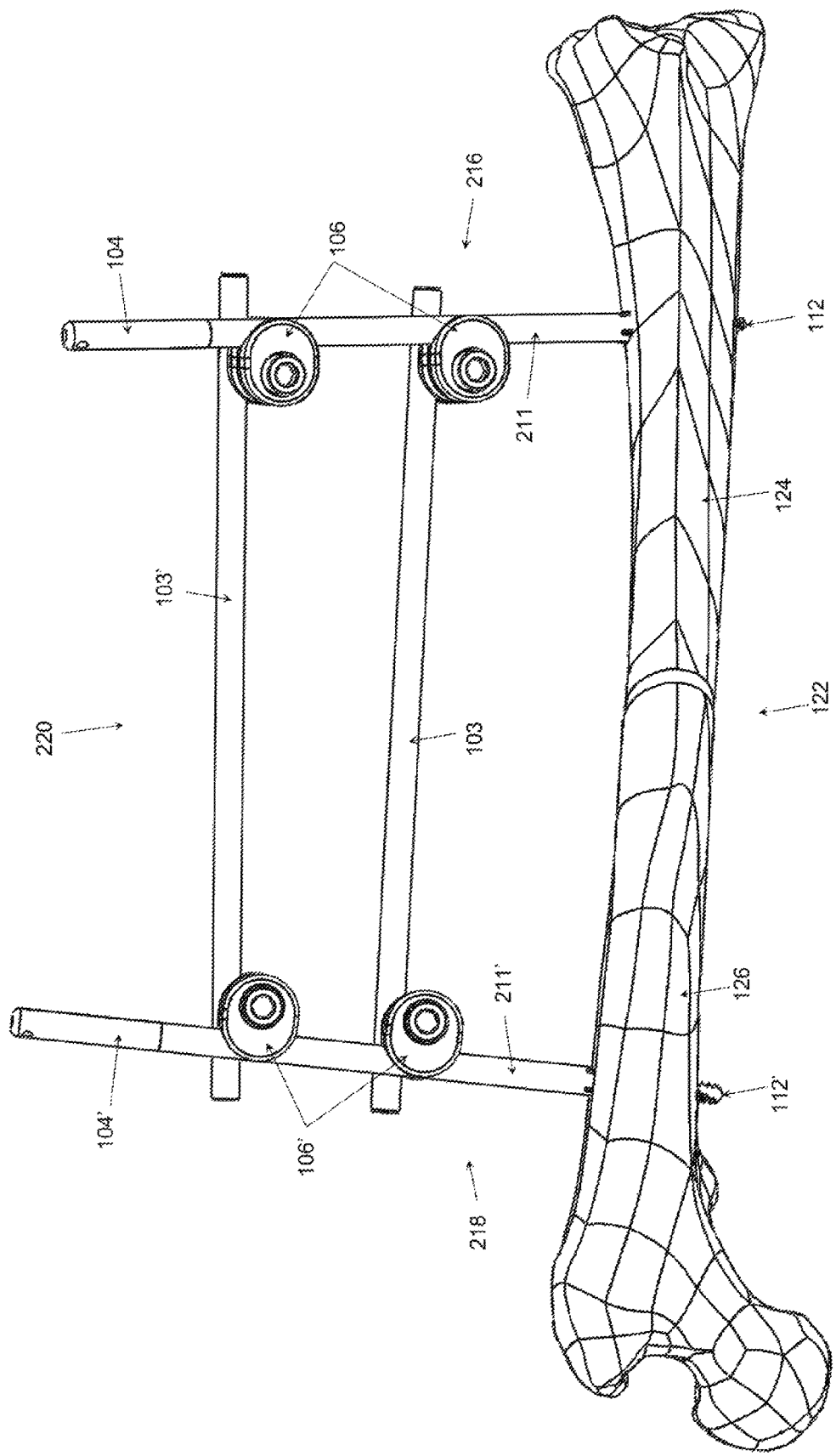
FIG. 3 shows a perspective view of an embodiment of an external fixation device fixated to a fractured bone.

In an additional embodiment, as best seen in FIG. 3, two rods 103, 103' connect distal pin assembly 116 to proximal pin assembly 118 by use of clamping grip provided by each clamp 106, 106', as previously described. Additional rods and clamps can be used to further stabilize the orthopedic external fixation device.

As shown in FIGS. 1-8, the two pin assemblies of each embodiment can be spaced apart along the rod-clamp system, such that the rod-clamp system forms a bridge between the pin assemblies. The rod-clamp system is desirably designed such that the spacing between the two pin assemblies can be adjusted and need not be planar or unilateral.

While various descriptions of the present invention are described above, it should be understood that the various features can be used singly or in any combination. Therefore, the present invention is not limited to only the specific embodiments depicted herein.

The word "illustrative" is used herein to mean serving as an example, instance, or illustration. Any aspect or design described herein as "illustrative" is not necessarily to be construed as preferred or advantageous over other aspects or designs. Further, for the purposes of this disclosure and unless otherwise specified, "a" or "an" means "one or more".

The foregoing description of illustrative embodiments of the invention has been presented for purposes of illustration and of description. It is not intended to be exhaustive or to limit the invention to the precise form disclosed, and modifications and variations are possible in light of the above teachings or may be acquired from practice of the invention. The embodiments were chosen and described in order to explain the principles of the invention and as practical applications of the invention to enable one skilled in the art to utilize the invention in various embodiments and with various modifications as suited to the particular use contemplated. It is intended that the scope of the invention be defined by the claims appended hereto and their equivalents.

What is claimed is:

1. A pin assembly for an orthopedic external fixation device, wherein the pin assembly is configured to engage a bone fragment, the pin assembly comprising:
   (i) a screw portion having a distal end configured to engage the bone fragment and a proximal end, wherein the screw portion includes an unthreaded portion between the distal end and the proximal end, and wherein the unthreaded portion includes a cutting section with one or more cutting edges; and
   (ii) a support sheath portion having an elongated channel with a proximal end and a distal end, wherein the distal end of the elongated channel is configured to engage the bone fragment, wherein the proximal end of the screw portion is disposed in the elongated channel, and wherein the distal end of the elongated channel has a tapered leading edge; and
   (iii) multiple elongated blades mounted to the distal end of the elongated channel such that the multiple elongated blades run lengthwise along an outer surface of the elongated channel, wherein the multiple elongated blades are configured to engage the bone fragment.

2. The pin assembly of claim 1, further comprising: (iv) a cap portion attached to the proximal end of the screw portion and engaged with the proximal end of the elongated channel of the support sheath portion.

3. The pin assembly of claim 1, wherein the multiple elongated blades comprises at least three elongated blades.

4. The pin assembly of claim 1, wherein the multiple elongated blades have sharp leading edges at their distal ends.

5. The pin assembly of claim 4, wherein the multiple elongated blades have triangular cross-sections.

6. The pin assembly of claim 5, wherein the multiple elongated blades have hollow ground surfaces.

7. The pin assembly of claim 1, wherein the multiple elongated blades have triangular cross-sections.

8. The pin assembly of claim 1, wherein the support sheath portion has a plurality of elongated slots defined in its distal end, the elongated slots being configured to allow the distal end of the support sheath portion to expand outwardly when it is passed over the screw portion.

9. The pin assembly of claim 1, wherein the distal end of the screw portion has a tip comprising a threaded section.

10. A method of engaging the pin assembly of claim 1 with a bone, the method comprising:
   a. engaging the distal end of the screw portion with the bone; and
   b. inserting the multiple elongated blades of the support sheath portion into the bone.

11. A pin assembly for an orthopedic external fixation device, wherein the pin assembly is configured to engage a bone fragment, the pin assembly comprising:
   (i) a screw portion having a distal end configured to engage the bone fragment and a proximal end, wherein the screw portion includes an unthreaded portion between the distal end and the proximal end, and wherein the unthreaded portion includes a cutting section with one or more cutting edges;
   (ii) a support sheath portion having an elongated channel with a proximal end and a distal end, wherein the distal end of the elongated channel is configured to engage the bone fragment, wherein the proximal end of the screw portion is disposed in the elongated channel; and
   (iii) multiple elongated blades running lengthwise along an outer surface of the elongated channel, wherein the multiple elongated blades are configured to engage the bone fragment, and wherein leading edges of the multiple elongated blades terminate at a leading edge of the distal end of the elongated channel.

12. A pin assembly for an orthopedic external fixation device, wherein the pin assembly is configured to engage a bone fragment, the pin assembly comprising:
   (i) a screw portion having a distal end configured to engage the bone fragment and a proximal end, wherein the screw portion includes an unthreaded portion between the distal end and the proximal end, and wherein the unthreaded portion includes a cutting section with one or more cutting edges;
   (ii) a support sheath portion having an elongated channel with a proximal end and a distal end, wherein the distal end of the elongated channel is configured to engage the bone fragment, wherein the proximal end of the screw portion is disposed in the elongated channel, and wherein an outer diameter at the distal end of the elongated channel is larger than an outer diameter of the distal end of the screw portion; and
   (iii) multiple elongated blades running lengthwise along an outer surface of the elongated channel, wherein the multiple elongated blades are configured to engage the bone fragment.

\* \* \* \* \*